US009622656B2

(12) United States Patent
Uchida

(10) Patent No.: US 9,622,656 B2
(45) Date of Patent: Apr. 18, 2017

(54) OPHTHALMOLOGICAL APPARATUS, COMPARISON METHOD, AND NON-TRANSITORY STORAGE MEDIUM

(71) Applicant: CANON KABUSHIKI KAISHA, Tokyo (JP)

(72) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 10 days.

(21) Appl. No.: 14/520,753

(22) Filed: Oct. 22, 2014

(65) Prior Publication Data

US 2015/0116664 A1 Apr. 30, 2015

(30) Foreign Application Priority Data

Oct. 24, 2013 (JP) ................. 2013-221088

(51) Int. Cl.
*A61B 3/00* (2006.01)
*A61B 3/10* (2006.01)
*A61B 3/14* (2006.01)

(52) U.S. Cl.
CPC ............. *A61B 3/0025* (2013.01); *A61B 3/00* (2013.01); *A61B 3/0041* (2013.01); *A61B 3/10* (2013.01); *A61B 3/102* (2013.01); *A61B 3/1005* (2013.01); *A61B 3/1025* (2013.01); *A61B 3/14* (2013.01)

(58) Field of Classification Search
CPC ... A61B 3/0025; A61B 3/0041; A61B 3/1005; A61B 3/102; A61B 3/1025; A61B 3/14; A61B 3/00; A61B 3/10
USPC ......................... 351/200, 205, 206
See application file for complete search history.

(56) References Cited

U.S. PATENT DOCUMENTS

| 5,868,134 A * | 2/1999 | Sugiyama ............. G06T 7/0012 600/300 |
| 7,884,945 B2 * | 2/2011 | Srinivasan ............. A61B 3/102 356/479 |
| 2003/0076477 A1 * | 4/2003 | Matsumoto ............ A61B 3/152 351/206 |
| 2007/0127033 A1 * | 6/2007 | Ueno ..................... A61B 3/102 356/497 |

(Continued)

FOREIGN PATENT DOCUMENTS

JP 5101975 B2 12/2012

*Primary Examiner* — Bumsuk Won
*Assistant Examiner* — William R Alexander
(74) *Attorney, Agent, or Firm* — Canon U.S.A., Inc. IP Division

(57) ABSTRACT

An ophthalmological apparatus includes a measurement unit configured to analyze a tomographic image and measure a layer thickness of a predetermined tissue of an eye being examined, a position identifying unit configured to identify positions of a plurality of parts of the eye being examined, a storage unit configured to store statistical data of layer thicknesses of the predetermined tissue of a plurality of eyes that have been examined, a position alignment unit configured to perform position alignment on an image of the eye being examined and an image represented by the statistical data, by using information regarding the positions of the plurality of parts, and a comparison unit configured to compare the layer thickness of the predetermined tissue of the eye being examined with the statistical data of the layer thicknesses of the predetermined tissue of the plurality of eyes that have been examined.

20 Claims, 17 Drawing Sheets

(56) References Cited

U.S. PATENT DOCUMENTS

| | | | | |
|---|---|---|---|---|
| 2009/0161827 A1* | 6/2009 | Gertner | ................... | A61F 9/008 |
| | | | | 378/65 |
| 2011/0046480 A1* | 2/2011 | Yonezawa | .............. | A61B 3/102 |
| | | | | 600/425 |
| 2012/0121158 A1* | 5/2012 | Sekine | ............... | G01N 21/4795 |
| | | | | 382/131 |
| 2012/0150029 A1* | 6/2012 | Debuc | .................... | A61B 3/102 |
| | | | | 600/425 |
| 2012/0281183 A1* | 11/2012 | Mousset | ........... | G01M 11/0228 |
| | | | | 351/159.77 |
| 2012/0287405 A1* | 11/2012 | Mousset | ........... | G01M 11/0228 |
| | | | | 351/246 |
| 2013/0195340 A1* | 8/2013 | Iwase | ................ | G06K 9/00617 |
| | | | | 382/131 |

* cited by examiner

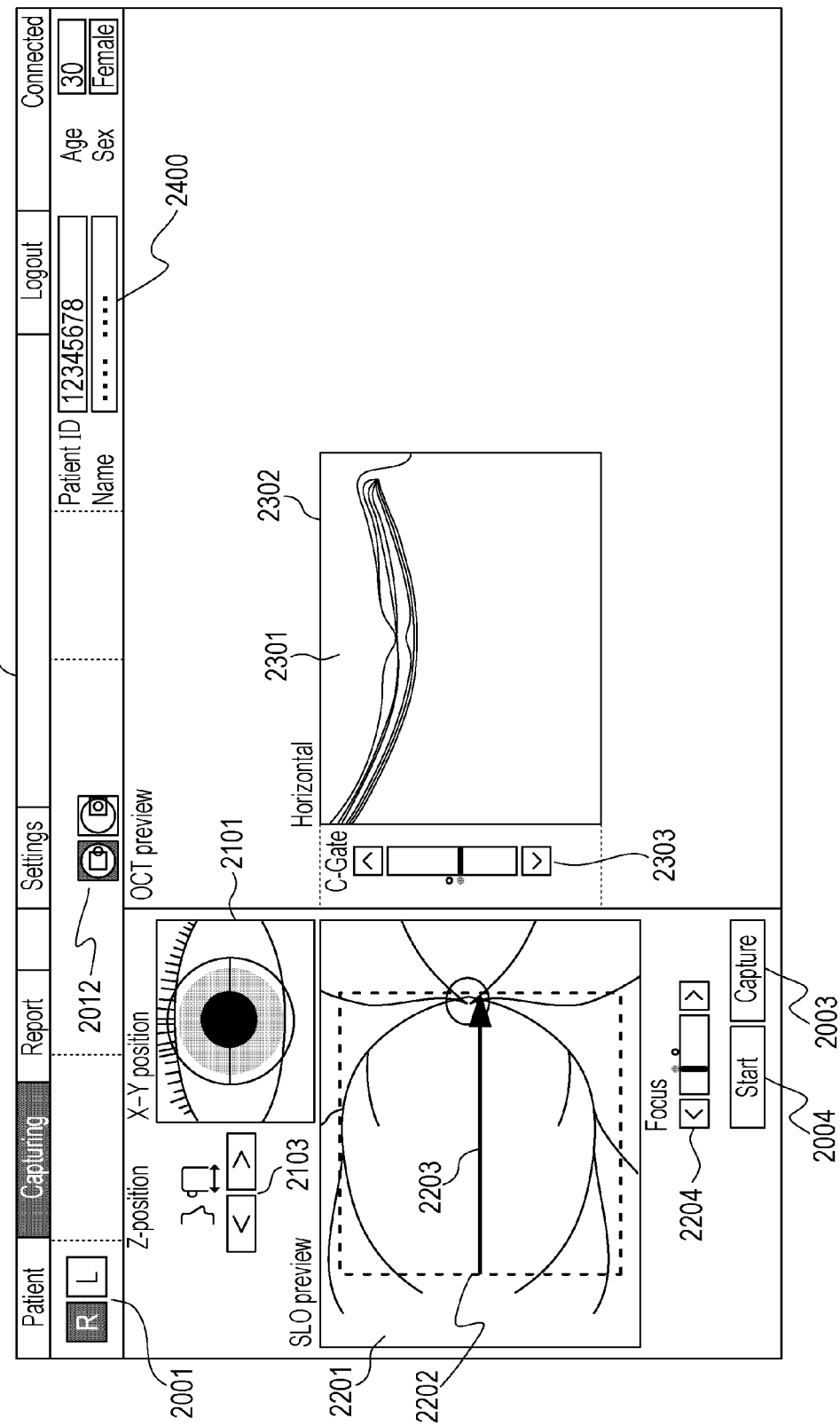

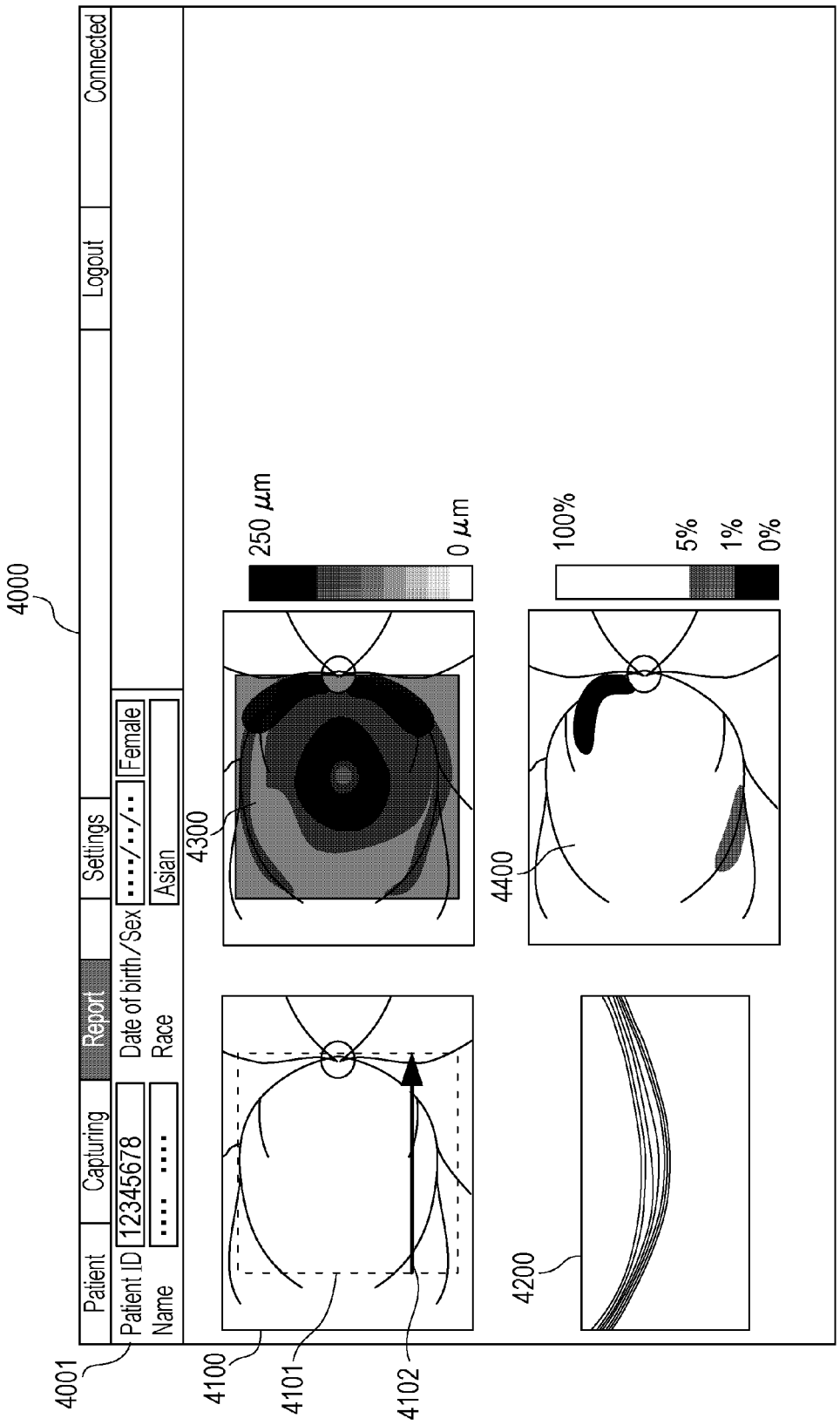

FIG. 6A
FIG. 6B
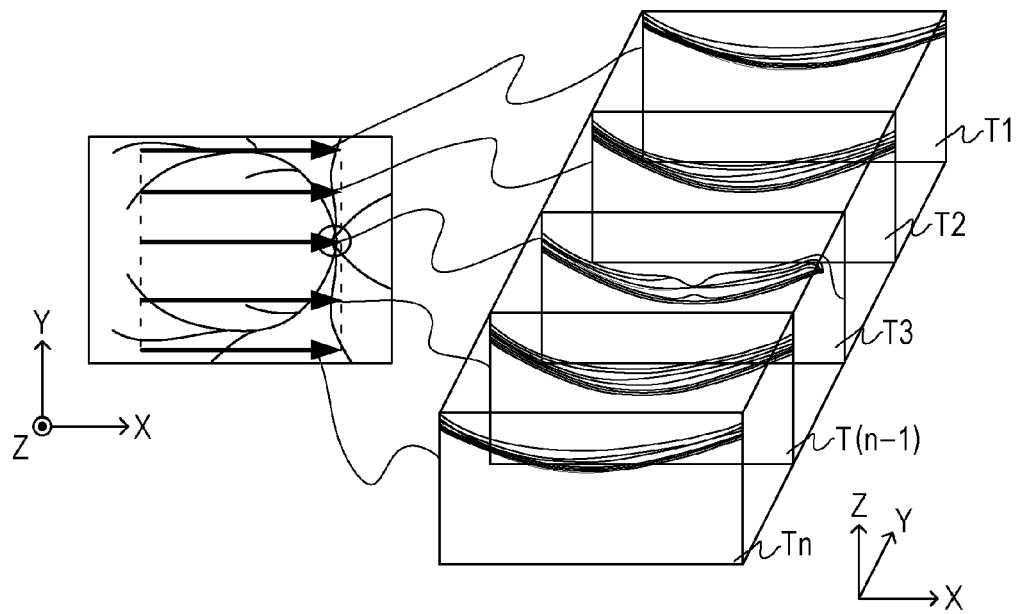
FIG. 6C
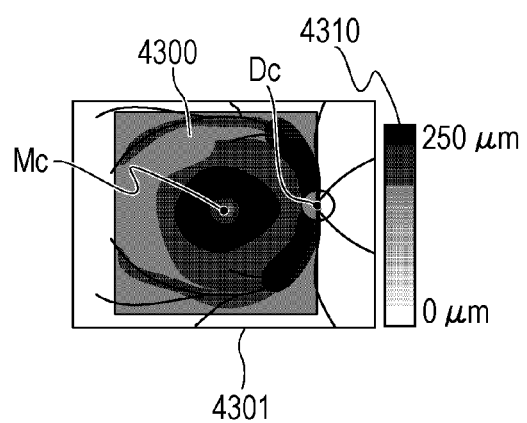

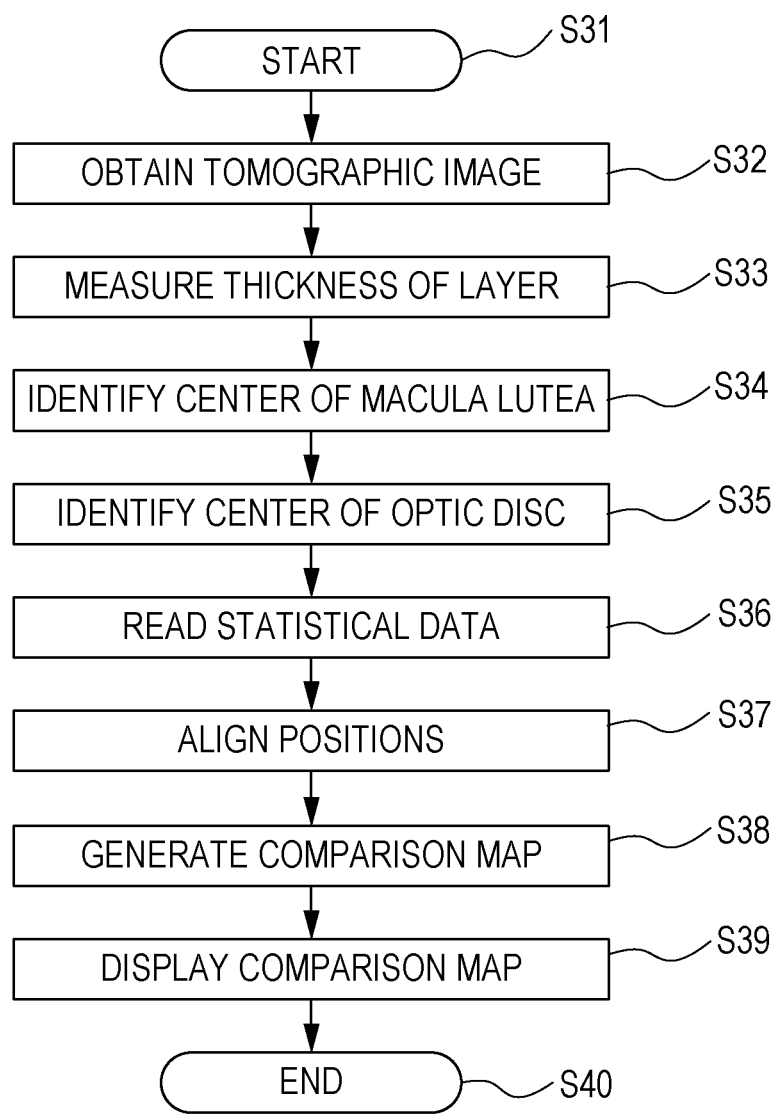

OPHTHALMOLOGICAL APPARATUS, COMPARISON METHOD, AND NON-TRANSITORY STORAGE MEDIUM

BACKGROUND OF THE INVENTION

Field of the Invention

The present invention relates to an ophthalmological apparatus, a comparison method, and a non-transitory storage medium.

Description of the Related Art

Currently, a tomographic image of an eye being examined can be obtained using optical coherence tomography (OCT) that utilizes multi-wavelength optical interference.

In addition, a comparison of a layer thickness obtained by analyzing a tomographic image with a reference layer thickness can contribute to the diagnosis of specific eye diseases. Further, as disclosed by Japanese Patent No. 5101975, a technique is available which contributes to the diagnosis of eye diseases by comparing a measured layer thickness with stored statistical data regarding layer thicknesses of healthy eyes that are free from eye diseases.

When statistical data of layer thicknesses of healthy eyes and the layer thickness obtained from a captured tomographic image are compared with each other, the comparison result may become inaccurate unless layer thicknesses at the same part are compared with each other. For this reason, an optical coherence tomography (OCT) apparatus described in Japanese Patent No. 5101975 determines a reference position and performs position alignment on images in accordance with the reference position, thereby enabling comparison of layer thicknesses at the same part.

However, appropriate comparison may not be performed in the case where only one piece of position information is used to perform position alignment on the captured tomographic image and an image represented by the statistical data of layer thicknesses of healthy eyes as in the above-described case.

SUMMARY OF THE INVENTION

In view of the issue described above, an aspect of the present invention aims to improve accuracy in comparison of a measured layer thickness with statistical data of layer thicknesses of healthy eyes.

An aspect of the present invention provides an ophthalmological apparatus including a generation unit configured to generate a tomographic image of an eye being examined, on the basis of interference light obtained by interference between reference light and returning light of light that has been radiated to the eye being examined; a measurement unit configured to analyze the tomographic image generated by the generation unit and measure a layer thickness of a predetermined tissue of the eye being examined; a position identifying unit configured to identify positions of a plurality of parts of the eye being examined; a storage unit configured to store statistical data of layer thicknesses of the predetermined tissue of a plurality of eyes that have been examined; a position alignment unit configured to perform position alignment on an image of the eye being examined and an image represented by the statistical data, by using information regarding the positions of the plurality of parts; and a comparison unit configured to compare the layer thickness of the predetermined tissue of the eye being examined with the statistical data of the layer thicknesses of the predetermined tissue of the plurality of eyes that have been examined.

Further features of the present invention will become apparent from the following description of exemplary embodiments with reference to the attached drawings.

BRIEF DESCRIPTION OF THE DRAWINGS

FIG. 3 is an illustrative diagram of a capture screen of the OTC apparatus according to the embodiment of the present invention.

FIG. 4 is an illustrative diagram of a report screen that displays an analysis result obtained in the case where an image has been captured by focusing on a macula lutea portion.

FIGS. 6A to 6C are diagrams illustrating a method for generating a layer-thickness map of the macula lutea portion.

FIG. 9 is a flowchart illustrating a method for aligning a position of an image showing a layer thickness of an eye being examined with a position of an image represented by the statistical data of layer thicknesses of healthy eyes.

DESCRIPTION OF THE EMBODIMENTS

Configuration of Main Body

An optical coherence tomography (OCT) apparatus according to an embodiment will be described below with reference to the accompanying drawings.

Figure 2A:
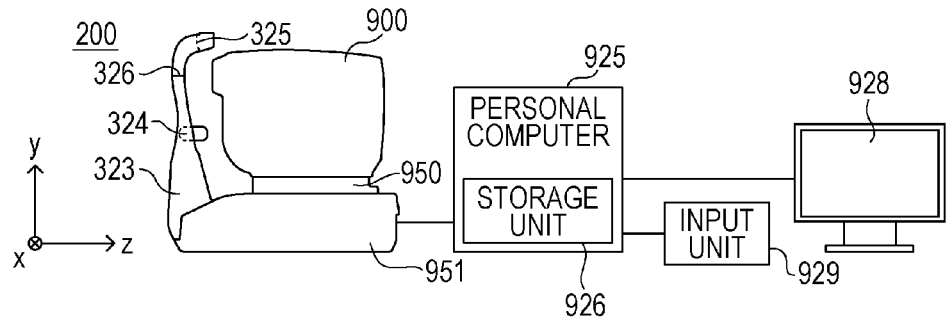
FIG. 2A is an overall schematic diagram of an optical coherence tomography (OCT) apparatus according to the embodiment of the present invention.

FIG. 2A is a lateral view of an OCT apparatus (ophthalmological apparatus) 200 according to this embodiment. The OCT apparatus 200 includes an obtaining unit (measurement optical system) 900, a stage portion 950, and a base portion 951. The obtaining unit 900 obtains images of an anterior-eye portion and front-view images (fundus images) and tomographic images of an eye being examined. The stage portion 950 serves as a moving portion and allows the obtaining unit 900 to move in the X-axis, Y-axis, and Z-axis directions using motors (not illustrated). The base portion 951 includes a spectroscope (described later).

The obtaining unit 900 scans a subject with light for obtaining an image of a subject and captures an image of the subject, thereby obtaining the image of the subject. This will be described in detail later.

The OCT apparatus 200 also includes a personal computer (PC) 925 and a storage unit 926 such as a hard disk drive. The PC 925 configures tomographic images, controls the stage portion 950, and performs control such as control of an alignment operation. The PC 925 also measures a layer thickness, identifies the center of the macula lutea, identifies the center of the optic disc, performs position alignment, generates a comparison map, and performs display control of a monitor (described later). The storage unit 926 serves as a patient information storage unit that stores information about patients and various pieces of captured image data, and as a storage unit that stores a tomographic image capturing program and statistical data of layer thicknesses of healthy eyes.

The OCT apparatus 200 also includes a display unit 928 such as a monitor, and an input unit 929 with which instructions are input to the PC 925. Specifically, the input unit 929 includes a keyboard and a mouse. The display unit 928 is a single common monitor that displays a capturing screen and a report screen (described later) in a time-division manner, and is included not in the obtaining unit 900 but in the PC 925.

The OCT apparatus 200 further includes a face rest 323. The face rest 323 includes a chin rest 324 and a forehead rest 325 which can be moved up and down by a motor (not illustrated), and a height-of-eye line 326 provided substantially at the center of a movable range of an objective (described later) in the height direction. The face of a subject is fixed so that an eye of the subject is located substantially as high as the height-of-eye line 326 by placing the chin of the subject on the chin rest 324 and placing the forehead of the subject against the forehead rest 325. In this way, the position of an eye to be examined can be substantially aligned with respect to the obtaining unit 900.

Block Diagram

Figure 2B:
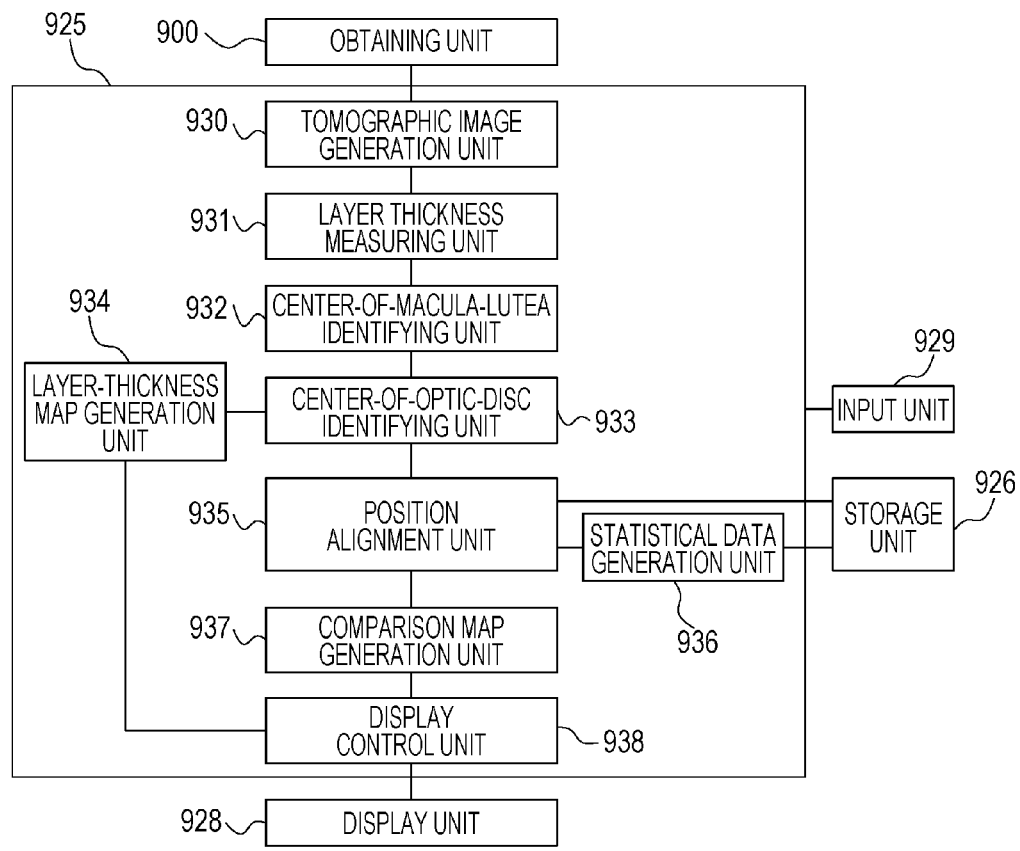
FIG. 2B is a block diagram of the OCT apparatus according to the embodiment of the present invention.

Referring to FIG. 2B, a block diagram according to this embodiment will be described. Details about individual operations will be described later.

A tomographic image generation unit 930 generates a tomographic image on the basis of a signal of reference light (described later) obtained by the obtaining unit 900.

A layer thickness measuring unit 931 analyzes the tomographic image generated by the tomographic image generation unit 930, identifies a layered structure of the eye being examined, and measures a thickness of a certain layer (layer thickness of a certain tissue). The layer thickness measuring unit 931 corresponds to an example of a measurement unit in accordance with one aspect of the present invention.

A center-of-macula-lutea identifying unit 932 identifies the position of the center of the macula lutea of the eye being examined, by using the tomographic image generated by the tomographic image generation unit 930, the layer thickness measured by the layer thickness measuring unit 931, and information on the position at which a fixation lamp is presented. The center-of-macula-lutea identifying unit 932 corresponds to one section of a position identifying unit in accordance with one aspect of the present invention.

A center-of-optic-disc identifying unit 933 identifies the position of the center of the optic disc of the eye being examined, by using the tomographic image generated by the tomographic image generation unit 930, the layer thickness measured by the layer thickness measuring unit 931, and a front-view image of the eye being examined. The center-of-optic-disc identifying unit 933 corresponds to one section of the position identifying unit in accordance with one aspect of the present invention.

A layer-thickness map generation unit 934 generates, using information on the measured layer thickness obtained by the layer thickness measuring unit 931, a colored map in which different layer thicknesses are represented in different colors.

A position alignment unit 935 aligns a position of an image of the eye being examined with a position of an image represented by the statistical data and aligns positions of images of a plurality of eyes that have been examined with one another, by using position information on the center of the macula lutea identified by the center-of-macula-lutea identifying unit 932 and position information on the center of the optic disc identified by the center-of-optic-disc identifying unit 933. The position alignment unit 935 corresponds to an example of a position alignment unit in accordance with one aspect of the present invention.

A statistical data generation unit 936 generates, as the statistical data, layer thickness information regarding a plurality of eyes that have been examined, positions of which have been aligned by using pieces of position information on the center of the macula lutea and the center of the optic disc.

A comparison map generation unit 937 compares the layer thickness of the eye being examined with the statistical data, and generates the comparison result as a colored map. The comparison map generation unit 937 corresponds to an example of a comparison unit in accordance with one aspect of the present invention.

A display control unit 938 performs control to display the colored maps generated by the layer-thickness map generation unit 934 and the comparison map generation unit 937 on the display unit (i.e., a monitor) 928.

Configurations of Measurement Optical System and Spectroscope

Figure 2C:
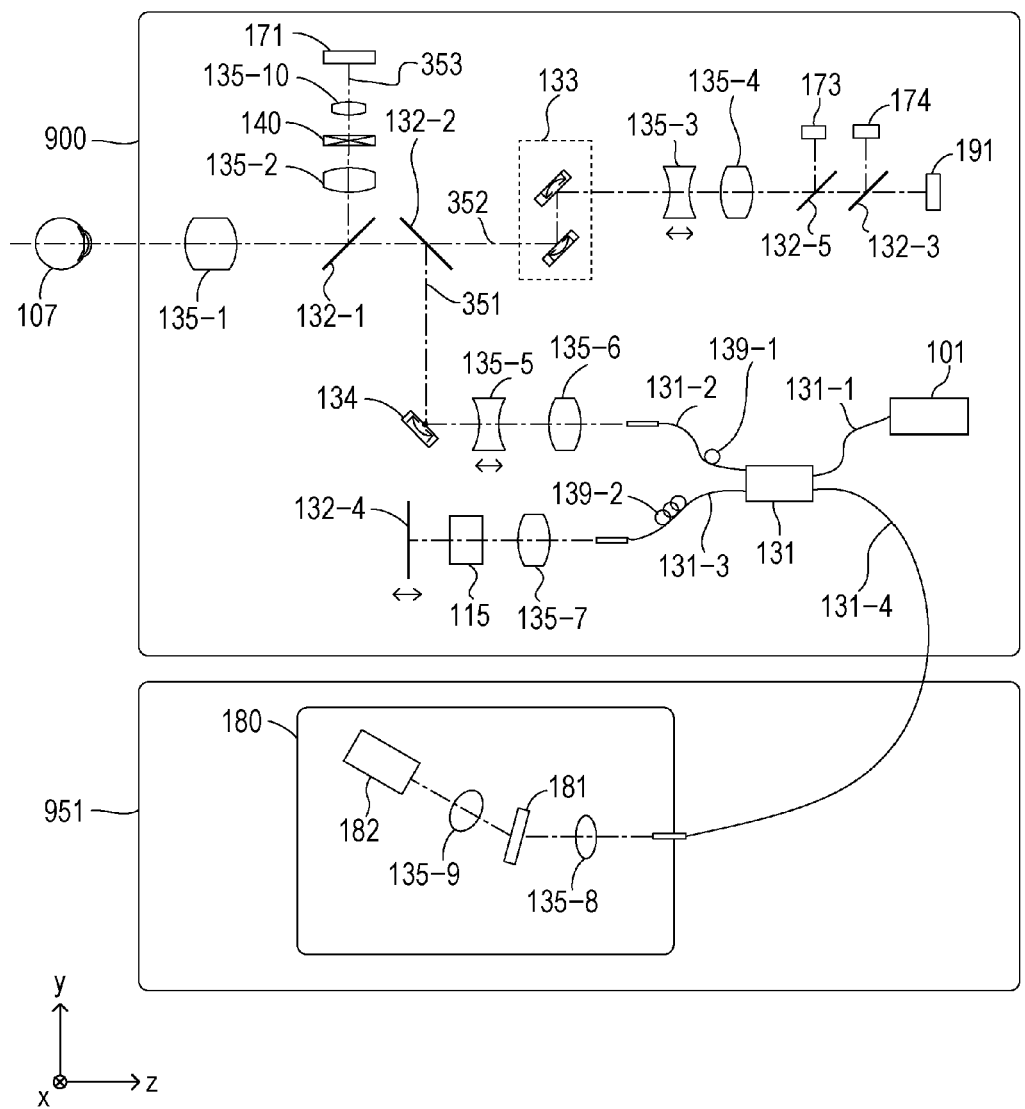
FIG. 2C is an illustrative diagram of a measurement optical system corresponding to an obtaining unit of the OCT apparatus according to the embodiment of the present invention.

Referring to FIG. 2C, configurations of the measurement optical system and the spectroscope used in this embodiment will be described. First, the internal configuration of the obtaining unit 900 will be described. The obtaining unit 900 includes an objective 135-1 which opposes an eye being examined 107. On the optical axis of the objective 135-1, a first dichroic mirror 132-1 and a second dichroic mirror 132-2 are arranged. The first and second dichroic mirrors 132-1 and 132-2 branch, based on wavelength bands, light to a first optical path 351 for an OCT optical system, a second optical path 352 for a fixation lamp and a scanning laser ophthalmoscope (SLO) optical system for observation and obtaining of a front-view image of the eye being examined 107, and a third optical path 353 for observation of the anterior eye portion.

The second optical path 352 for the fixation lamp and the SLO optical system includes an SLO scanning unit 133, lenses 135-3 and 135-4, a mirror 132-5, a third dichroic mirror 132-3, a photodiode 173, an SLO light source 174, and a fixation lamp 191. The mirror 132-5 is a prism vapor-deposited with a perforated mirror or a mirror with a hollow, and separates light illuminated by the SLO light source 174 and returning light from the eye being examined 107 from each other. The third dichroic mirror 132-3 splits, based on wavelength bands, light to an optical path to the SLO light source 174 and an optical path to the fixation lamp 191. The SLO scanning unit 133 scans the eye being examined 107 with light emitted from the SLO light source 174 and the fixation lamp 191, and includes an X-scanner that performs scanning in the X-axis direction and a Y-scanner that performs scanning in the Y-axis direction. In this embodiment, the X-scanner includes a polygon mirror because high-speed scanning is desired, whereas the Y-scanner includes a galvano mirror. The lens 135-3 is driven by a motor (not illustrated) in order to adjust the focal-points of the SLO optical system and the fixation lamp 191. The SLO light source 174 emits light of a wavelength of approximately 780 nm. The photodiode 173 detects returning light from the eye being examined 107. The fixation lamp 191 emits visible light and prompts the subject to do fixation.

Light emitted from the SLO light source 174 is reflected by the third dichroic mirror 132-3, passes through the mirror 132-5, passes through the lenses 135-4 and 135-3, and is used by the SLO scanning unit 133 to scan the eye being examined 107. Returning light from the eye being examined 107 propagates along the same path as that of the emitted light, is reflected by the mirror 132-5, and is led to the photodiode 173. Light emitted from the fixation lamp 191 passes through the third dichroic mirror 132-3 and the mirror 132-5, passes through the lenses 135-4 and 135-3, and is used by the SLO scanning unit 133 to scan the eye being examined 107. At this time, the fixation lamp 191 is caused to blink in accordance with movement of the SLO scanning unit 133 to form a given shape at a given position on the eye being examined 107. In this way, the subject is prompted to do fixation.

The third optical path 353 for observation of the anterior eye portion includes lenses 135-2 and 135-10, a split prism 140, and a charge coupled device (CCD) 171 that detects infrared to observe the anterior eye portion. This CCD 171 has a sensitivity to a wavelength of anterior-eye observation light (not illustrated), specifically, a wavelength of approximately 970 nm. The split prism 140 is arranged at a conjugate position of the pupil of the eye being examined 107, and is capable of detecting, as a split image of the anterior eye portion, a distance in the Z-axis direction (back-and-forth direction) of the obtaining unit 900 relative to the eye being examined 107.

The first optical path 351 for the OCT optical system forms an OCT optical system as described before, and is used to capture a tomographic image of the eye being examined 107. More specifically, the first optical path 351 is used to obtain an interference signal for forming a tomographic image. The first optical path 351 includes an X-Y scanner 134 that scans the eye being examined 107 with light. Although the X-Y scanner 134 is illustrated as a single mirror, it is a galvano mirror that performs scanning in directions of two (X and Y) axes.

The first optical path 351 also includes lenses 135-5 and 135-6. Among these lenses, the lens 135-5 is driven by a motor (not illustrated) to focus light from an OCT light source 101 which is emitted from an optical fiber 131-2 connected to an optical coupler 131 onto the eye being examined 107. As a result of this focusing, returning light from the eye being examined 107 simultaneously forms a spot-like image and enters the end of the optical fiber 131-2.

Now, configurations of an optical path from the OCT light source 101, a reference optical system, and the spectroscope will be described. The obtaining unit 900 further includes the OCT light source 101, a reference mirror 132-4, a dispersion compensation glass 115, the optical coupler 131, optical fibers 131-1 to 131-4 which are single-mode optical fibers connected to and integrated into the optical coupler 131, and a lens 135-7. A spectroscope 180 is also provided.

These components form the Michelson interference system. Light emitted from the OCT light source 101 passes through the optical fiber 131-1, and is split, by the optical coupler 131, into measurement light which goes to the optical fiber 131-2 and reference light which goes to the optical fiber 131-3. The measurement light passes through the above-described first optical path 351 for the OCT optical system and is radiated to the eye being examined 107 which is an observation target, and then reaches the optical coupler 131 through the same optical path as a result of reflection and dispersion caused by the eye being examined 107.

The measurement light and the reference light are superimposed by the optical coupler 131 to form interference light. Here, when the optical length of the measurement light is substantially equal to the optical length of the reference light, interference occurs. The reference mirror 132-4 is held to be adjustable in the optical-axis direction by a motor (not illustrated) and a driving mechanism (not illustrated), and is capable of making the optical length of the reference light substantially equal to the optical length of the measurement light which varies depending on the eye being examined 107. The interference light is led to the spectroscope 180 through the optical fiber 131-4.

A first polarization adjusting unit 139-1 for the measurement light is provided in the optical fiber 131-2. A second polarization adjusting unit 139-2 for the reference light is provided in the optical fiber 131-3. The first and second polarization adjusting units 139-1 and 139-2 have several loop-shaped windings of optical fiber. This loop-shaped portion is made wind around the longitudinal direction of the optical fiber to cause twisting of the optical fiber. In this way, polarization states of the measurement light and the reference light are adjusted to be substantially equal.

The spectroscope 180 includes lenses 135-8 and 135-9, a diffraction grating 181, and a line sensor 182. The interference light emitted from the optical fiber 131-4 passes through the lens 135-8 to become parallel light, is then split by the diffraction grating 181, and forms an image on the line sensor 182 via the lens 135-9.

The OCT optical system described above corresponds to an obtaining unit configured to radiate measurement light to an object being examined and to obtain a tomographic image in accordance with one aspect of the present invention.

Now, a configuration around the OCT light source 101 will be described. The OCT light source 101 is a super luminescent diode (SLD) which is a typical low-coherent light source. The OCT light source 101 has a center wavelength of 855 nm and a wavelength bandwidth of approximately 100 nm. Here, the bandwidth influences the resolution of the resulting tomographic image in the optical-axis direction and is an important parameter.

The SLD is selected here as the light source; however, any type of light source can be used as long as it can emit low-coherent light, and amplified spontaneous emission (ASE) or the like can be used. The center wavelength is suitably that of near infrared light by considering that measurement is performed on an eye. Also, because the center wavelength influences the resolution of the resulting tomographic image in the horizontal direction, a shorter wavelength is desired. From both of the above reasons, a center wavelength of 855 nm is selected.

In this embodiment, the Michelson interference system is used as the interference system; however, the Mach-Zehnder interference system may be used. Depending on a difference in light quantity between the measurement light and the reference light, the Mach-Zehnder interference system is desirably used when the difference in light quantity is large, and the Michelson interference system is desirably used when the difference in light quantity is relatively small.

With the configuration described above, tomographic images of an eye being examined can be obtained and high-contrast front-view images of the eye being examined can be obtained even using near infrared light.

Tomographic Image Capturing Method

A tomographic image capturing method using the OCT apparatus 200 will be described. The OCT apparatus 200 is capable of capturing a tomographic image of a predetermined part of the eye being examined 107 by controlling the X-Y scanner 134 thereof. Herein, a locus along which the eye being examined 107 is scanned with light for tomographic image capturing is referred to as a scan pattern. Examples of this scan pattern include cross scanning in which scanning is performed with respect to one point in a cross-shaped manner, and 3D-scanning in which scanning is performed to cover the whole area to obtain a three-dimensional (3D) tomographic image (volume image) as a result. In the case where detailed observation of a specific part is desired, cross-scanning is suitable. In the case where observation of the layered structure and a layer thickness of the entire retina is desired, 3D-scanning is suitable.

Herein, an image capturing method in the case of executing 3D-scanning will be described. First, a scan is performed using the measurement light in the X-axis direction in the drawings, and a predetermined number of captured image lines are obtained by the line sensor 182 from an X-axis-direction image capturing range of the eye being examined 107. Fast Fourier transform (FFT) is performed on a brightness distribution of the line sensor 182 obtained at a given position in the X-axis direction, and the linear brightness distribution resulting from FFT is converted into density information in order to display it on the display unit (i.e., a monitor) 928. The resulting image is referred to as an A-scan image.

Also, a two-dimensional image obtained by arranging a plurality of A-scan images is referred to as a B-scan image. A plurality of A-scan images forming one B-scan image are captured and then the Y-axis-direction scan position is moved and scanning is performed in the X-axis direction again. In this way, a plurality of B-scan images are obtained.

A plurality of B-scan images or a 3D image (volume data) constructed from a plurality of B-scan images is displayed on the display unit (i.e., a monitor) 928 (described later), so that the image is used by a checker to make a diagnosis on the eye being examined 107. Herein, an example of obtaining a 3D image by capturing a plurality of X-axis-direction B-scan images has been described; however, a 3D image may be obtained by capturing a plurality of Y-axis-direction B-scan images.

At this time, because of characteristics of Fourier transform based on its principles, a tomographic image which is symmetric about a specific position, specifically, a position (gate position) at which the optical length of the measurement light is substantially equal to the optical length of the reference light. Also, a periodical tomographic image with respect to the gate position is formed. Accordingly, in order to make the tomographic images easy-to-observe images for the checker, a specific region (image region) is desirably clipped and displayed.

Configuration of Capturing Screen

Referring to FIG. 3, a capturing screen 2000 according to this embodiment will be described. The capturing screen 2000 is a screen on which various settings and adjustments are made to obtain a desired image of an eye to be examined, and is a screen displayed on the display unit (i.e., a monitor) 928 before capturing is performed.

A patient information display portion 2400 displays information on a patient subjected to capturing using this screen, and displays, for example, the patient ID and the patient's name, age, and sex. A right-left eye switching button 2001 allows the obtaining unit 900 to be moved to an initial position set for the right or left eye when an L-button or an R-button is pressed. An anterior-eye-portion observation screen 2101 displays an image which is obtained by the CCD 171 for anterior-eye-portion observation. When a given point on the anterior-eye-portion observation screen 2101 is clicked with a mouse, the obtaining unit 900 is moved such that the clicked point becomes the center of the screen and is aligned with the position of the eye being examined 107. A scan mode selection button 2012 allows the user to select a macula-lutea 3D mode and an optic-disc 3D mode. A front-view image display screen 2201 displays a front-view image of the eye being examined 107 that is obtained by the photodiode 173. A tomographic image display screen 2301 is a screen used to check the obtained tomographic image. When a start button 2004 is pressed, capturing of a tomographic image and a front-view image is started, and the captured images of the eye being examined 107 are displayed on the front-view image display screen 2201 and the tomographic image display screen 2301 in real time. At this time, a frame 2202 displayed within the front-view image display screen 2201 indicates a range in which a tomographic image is obtained during capturing. Also, a horizontal arrow line 2203 located at the central portion in the vertical direction indicates the position on the eye being examined 107 at which the tomographic image displayed on the tomographic image display screen 2301 is obtained and the scanning direction.

Here, an outer frame 2302 of the tomographic image display screen 2301 indicates an image region. The left and right sides of the outer frame 2302 indicating the image region in FIG. 3 indicate the same boundaries as those of the frame 2202 indicating the scan range, its upper side indicates a position (gate position) at which the optical length of the measurement light is substantially equal to the optical length of the reference light, and its lower side indicates a position separate from the upper side by a predetermined length.

A slider arranged in the vicinity of each image is used to perform adjustment. A slider 2103 is used to adjust the Z-axis-direction position of the obtaining unit 900 relative to the eye being examined 107. A slider 2204 is used to adjust focus. A slider 2303 is used to adjust the position of the coherence gate. Focus is adjusted by moving the lenses 135-3 and 135-5 in the illustrated direction in order to focus on the fundus. The coherence gate is adjusted by moving the reference mirror 132-4 in the illustrated direction in order to permit observation of the tomographic image at a desired position of the tomographic image display screen 2301. Because this adjustment changes the difference in optical length between the optical path for the tomographic image and the reference optical path in the OCT optical system, the tomographic image displayed in the tomographic image display screen 2301 changes to an image of an upper or lower portion. Thus, the checker can arrange a tomographic image of a desired position in the tomographic image display screen 2301.

Through these adjustment operations, the checker creates a state enabling optimum image capturing. By pressing a capture button 2003 after various adjustments have been finished, desired image capturing is performed.

Configuration of Report Screen for Macula Lutea Portion

Referring to FIG. 4, a macula lutea report screen 4000 according to this embodiment will be described. The macula lutea report screen 4000 is a screen displayed on the display unit (i.e., a monitor) 928. The macula lutea report screen 4000 is a screen on which an image of the eye being examined 107 that has been captured after selecting the macula-lutea 3D mode using the scan mode selection button 2012, a measurement result, and a comparison result are checked in detail.

A patient information display portion 4001 displays information on a patient subjected to displaying in this screen, and displays, for example, the patient ID and the patient's name, date of birth, sex, and race. A front-view image display screen 4100 displays an SLO image or a projection image which is an image of the eye being examined 107 that has been reconstructed or reconfigured from the obtained tomographic image. A tomographic image display screen 4200 displays the obtained tomographic image. The locus of scanning performed when the tomographic image displayed on the tomographic image display screen 4200 is obtained is superimposed as an arrow 4102 on the front-view image display screen 4100. A frame 4101 displayed within the front-view image display screen 4100 indicates a range in which the tomographic image is obtained during capturing, and is a 10-mm×10-mm square centered at the macula lutea.

A layer-thickness map 4300 and a comparison map 4400 are also displayed. These maps will be described in detailed below.

Layer-thickness Map of Macula Lutea Portion

Referring to FIGS. 6A to 6C, the layer-thickness map according to this embodiment will be described.

Figure 16:
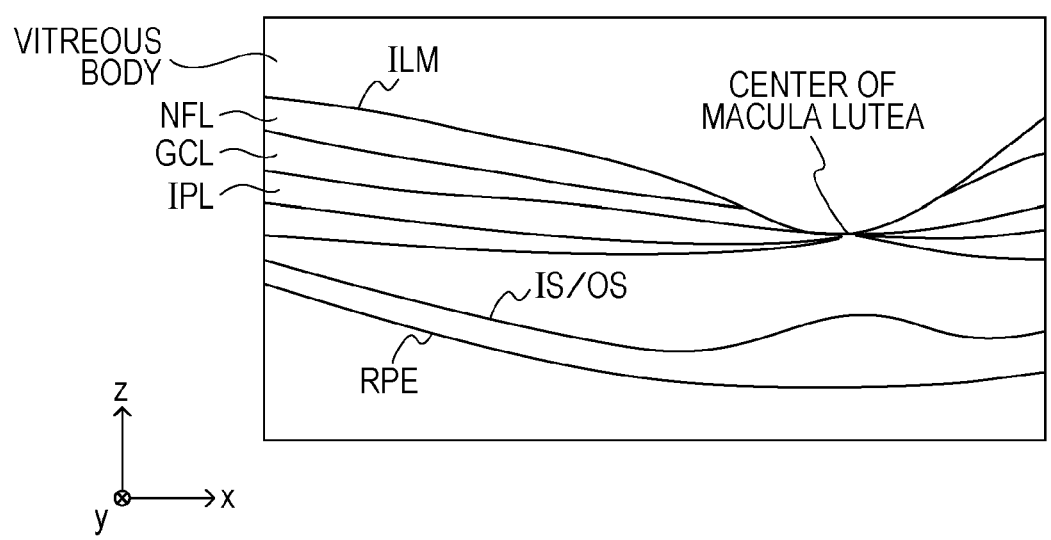
FIG. 16 is a diagram illustrating a layered structure of the retina.

As illustrated in FIG. 16, a human retina has layers called the vitreous body, the internal limiting membrane (ILM), the optic nerve fiber layer (NFL), the ganglion cell layer (GCL), the inner plexiform layer (IPL), the photoreceptor cell inner segment-outer segment junction (IS/OS), and the retinal pigmented epithelium (RPE).

It is known that thickness of each layer changes as a specific eye disease progresses. In particular, to make a diagnosis of glaucoma, it is important to observe thicknesses of layers including NFL and GCL. A colored map called a layer-thickness map in which different layer thicknesses at individual positions on the retina are represented in different colors is effective to observe the layer thickness. Because a magnitude of the layer thickness is represented as a change in color, the layer-thickness map allows the user to intuitionally understand the position where the layer thickness is increased or decreased. As layer-thickness maps for use in the diagnosis of glaucoma, an NFL thickness map, a total layer-thickness map of NFL, GCL, and IPL, and a total layer-thickness map of GCL and IPL are typically used, for example. In particular, as the layer-thickness map of the macula lutea portion, a total layer-thickness map of NFL, GCL, and IPL and a total layer-thickness map of GCL and IPL are used. A reason for this is that nerve cells are distributed in a donut-like shape around the center of the macula lutea.

Referring to FIGS. 6A to 6C, a layer-thickness map will be described. FIG. 6C is a schematic diagram of a layer-thickness map. FIG. 6C illustrates a two-dimensional image 4301, the layer-thickness map 4300, and a color scale 4310 indicating a color corresponding to a layer thickness. In the region of the layer-thickness map 4300, a layer thickness based on a result of layer thickness analysis of a specific layer is represented in a color based on the color scale 4310. This allows the user to easily and intuitively observe a distribution of layer thicknesses and efficiently make a diagnosis. Note that in FIG. 6C, a semi-transparent color is used and the layer-thickness map 4300 is superimposed on a front-vide image.

Figure 5:
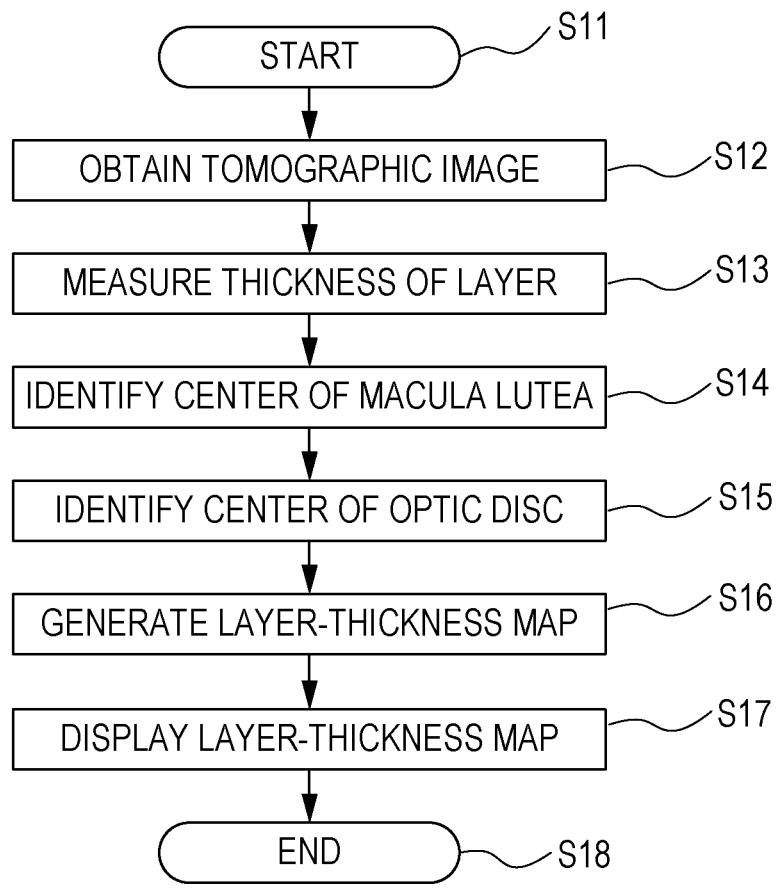
FIG. 5 is a flowchart illustrating a method for generating a layer-thickness map.

Referring next to FIG. 5, a flow of a process for generating a layer-thickness map in accordance with this embodiment will be described. After the process is started in step S11, the obtaining unit 900 obtains volume data of tomographic images and the tomographic image generation unit 930 generates tomographic images in step S12. Then, the layer thickness measuring unit 931 analyzes a layered structure of the eye being examined 107 in step S13. In analysis of the layered structure, the individual layers can be identified based on the fact that a signal intensity changes due to a different reflectance of each layer. After performing analysis of the layered structure, the layer thickness measuring unit 931 measures a thickness of each layer.

Then in step S14, the center-of-macula-lutea identifying unit 932 identifies the position of the center of the macula lutea. The volume data of tomographic images generated in step S12 is composed of a plurality of tomographic images including the macula lutea portion as illustrated in FIGS. 6A and 6B. Accordingly, the center-of-macula-lutea identifying unit 932 uses the results of layer thickness measurement performed on the plurality of tomographic images, and decides, as the center of the macula lutea, a position at which a total layer thickness of NFL, GCL, and IPL is the smallest. The center of the macula lutea is also called fovea and is the center of the field of view, and appears as a dip of ILM in a tomographic image as illustrated in FIG. 16. It is also known that, among the layers that form the retina, upper layers called an inner layer is very thin under the center of the macula lutea. Accordingly, the center of the macula lutea can be determined by identifying the position at which a total layer thickness of NFL, GCL, and IPL which are some of the upper layers is small. Note that because every layer of the retinal inner layers gets thinner under the center of the macula lutea, the center of the macula lutea can be identified using not only the total layer thickness of NFL, GCL, and IPL but also a layer thickness of NFL alone, a total layer thickness of GCL and IPL, and a layer thickness of IPL.

Further, the center-of-macula-lutea identifying unit 932 may identify the position of the center of the macula lutea using information on the position where the fixation lamp 191 is presented. When a tomographic image is captured, the eye being examined 107 stares at the fixation lamp 191. As described above, because the center of the macula lutea is the center of the field of view, the center-of-macula-lutea identifying unit 932 can identify the position at which the fixation lamp 191 is presented as the center of the macula lutea. Alternatively, the center-of-macula-lutea identifying unit 932 may identify the position of the macula lutea instead of the center of the macula lutea. Alternatively, the center-of-macula-lutea identifying unit 932 may identify the barycenter instead of the center of the macula lutea.

Then in step S15, the center-of-optic-disc identifying unit 933 identifies the position of the center of the optic disc. The center-of-optic-disc identifying unit 933 identifies a position of a circular portion not having the RPE layer by using results of layer thickness measurement performed on the plurality of tomographic images, and decides the center of the circular portion as the center of the optic disc. The optic disc is a large dip on the retina. This dip allows many blood vessels and optic nerves to pass therethrough from outside the retina, and the layered structure of RPE and the like is not seen within this dip. Accordingly, by identifying a part at which the RPE layer is absent, the position of the center of the optic disc can be identified. Also, the position of the center of the optic disc can be identified using a front-view image of the retina. The optic disc portion appears as a circular area having a very high brightness in a front-view image of the retina. Accordingly, the shape of the optic disc is recognized through image processing such as edge detection and binarization, and the position of the center of the optic disc can be identified. Alternatively, the center-of-optic-disc identifying unit 933 may identify the position of the optic disc instead of the center of the optic disc. Alternatively, the center-of-optic-disc identifying unit 933 may identify the barycenter instead of the center of the optic disc.

Then in step S16, the layer-thickness map generation unit 934 generates layer-thickness map data on the basis of the layer thicknesses obtained in step S13. After the layer-thickness map data has been generated in step S16, the layer-thickness map is displayed on the macula lutea report screen 4000 in step S17. The process then ends in step S18.

Statistical Data of Macula Lutea Portion

Figure 8A:
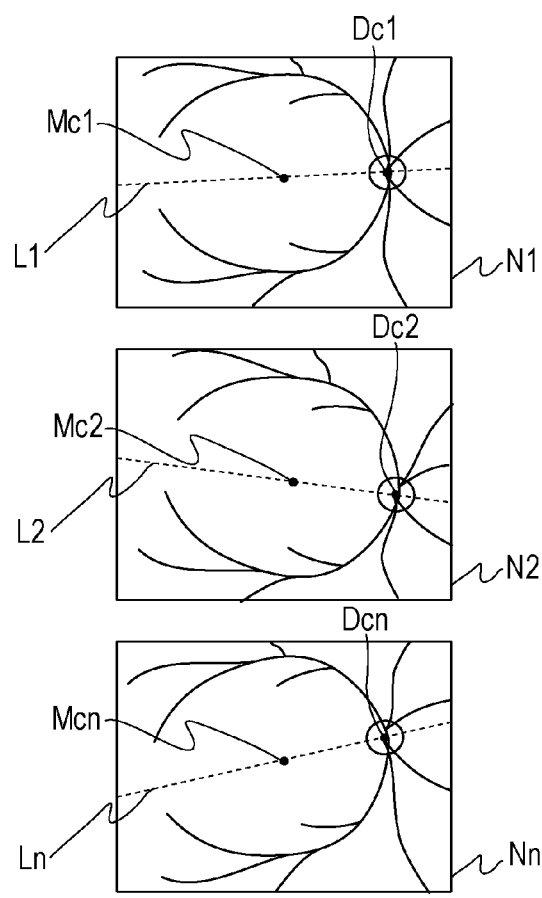
FIGS. 8A to 8C are diagrams illustrating a method for generating statistical data of layer thicknesses of the macula lutea portion.
Figure 8B:
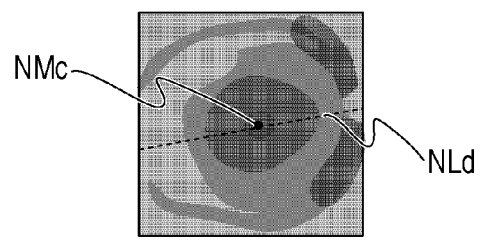
Figure 8C:
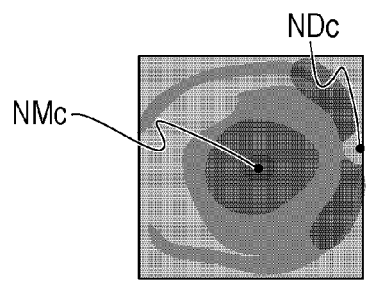

Referring next to FIGS. 8A to 8C, a method for generating statistical data for use in comparison of layer thickness will be described. The statistical data is statistical data of layer thicknesses of a plurality of examined eyes selected based on a certain criterion and is often statistical data of layer thicknesses of healthy eyes free from eye diseases. When layer thicknesses of many healthy eyes are measured, the distribution of the obtained layer thicknesses has a certain width. When this width is considered as a normal distribution, a 98%-confidence interval or 90%-confidence interval relative to a population can be determined. By comparing the actual layer thickness of a patient with the confidence interval, it can be determined whether the layer thickness of the patient deviates from the normal range. In particular, in the case of glaucoma, a comparison of the layer thickness of NFL and GCL with the statistical data can contribute to the early diagnosis of glaucoma.

The layer thickness of NFL and GCL of the retina is related to a distribution of optic nerves and how optic nerves run. Optic nerves radially extend from the optic disc portion, and run like an arc to surround the center of the macula lutea. Accordingly, the layer thickness of NFL and GCL greatly depends on the positional relationship between the optic disc portion and the center of the macula lutea. On the other hand, as illustrated in FIG. 8A, the positional relationship between the optic disc portion and the center of the macula lutea greatly differs from person to person. Accordingly, when statistical data of layer thicknesses is generated, it is important to take the positional relationship between the optic disc portion and the center of the macula lutea into consideration.

Figure 7:
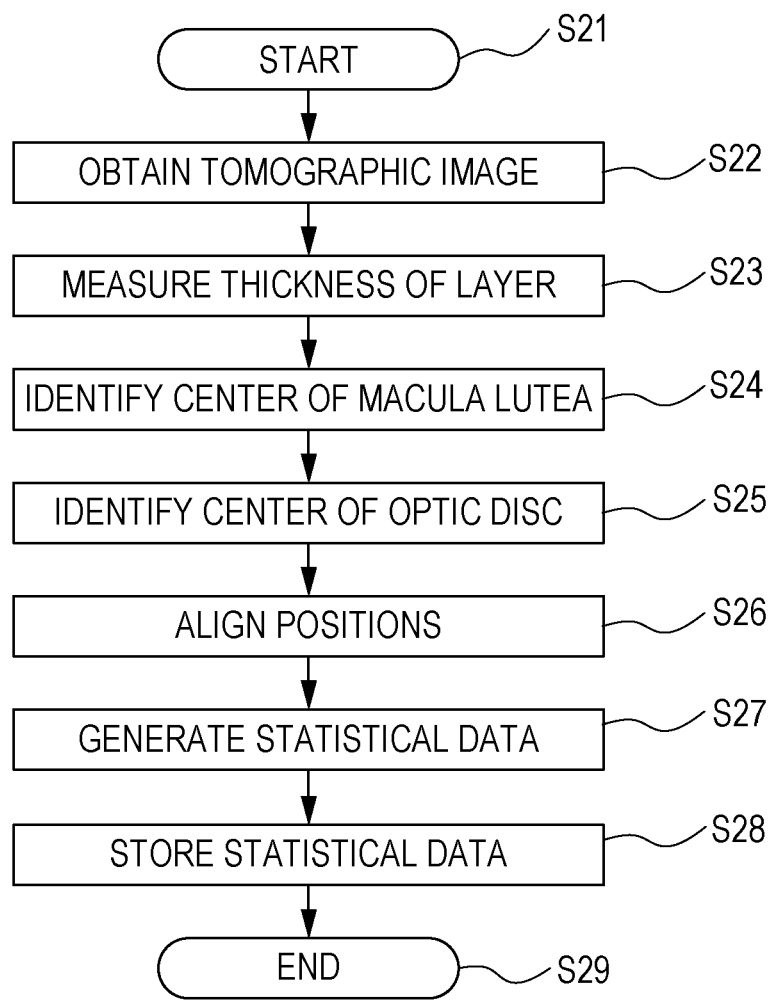
FIG. 7 is a flowchart illustrating a method for generating statistical data of layer thicknesses.

Referring next to FIG. 7, a flow of a process for generating statistical data according to this embodiment will be described. First, after the process is started in step S21, the obtaining unit 900 obtains volume data of tomographic images and the tomographic image generation unit 930 generates tomographic images in step S22. Then in step S23, the layer thickness measuring unit 931 analyzes the layered structure of the eye being examined 107. After analyzing the layered structure, the layer thickness measuring unit 931 measures layer thicknesses of the individual layers. Then in step S24, the center-of-macula-lutea identifying unit 932 identifies the position of the center of the macula lutea. In step S25, the center-of-optic-disc identifying unit 933 identifies the position of the center of the optic disc. A series of steps up to this step is the same as that performed when the layer-thickness map is generated. A series of steps from step S22 to step S25 is performed on a plurality of examined eyes, whereby pieces of information on the layer thickness, the center of the macula lutea, and the center of the optic disc of the plurality of examined eyes are obtained.

Then in step S26, the position alignment unit 935 performs position alignment on images showing the layer thicknesses of the plurality of examined eyes. First, the position alignment unit 935 aligns positions of the center of the macula lutea Mc1, Mc2, . . . , Mcn illustrated in FIG. 8A. This position alignment is performed by translating the images represented by pieces of data in the horizontal and vertical directions so that the positions of the center of the macula lutea in all the images substantially coincide with one another. Then, the position alignment unit 935 aligns positions of the center of the optic disc Dc1, Dc2, . . . , Dcn. This position alignment is performed by rotating the images represented by the pieces of data about the center of the macula lutea so that inclinations of lines L1, L2, . . . , Ln extending from the center of the macula lutea Mcn toward the center of the optic disc Dcn are substantially equal to one another. That is, position alignment is performed in the rotational direction. As a result of these position alignments, all the images represented by the pieces of data share a center-of-macula-lutea position NMc and a matching line NLd extending toward the center of the optic disc as illustrated in FIG. 8B. Thus, highly reliable statistical data can be generated.

In another embodiment of position alignment, position alignment may be performed such that positions of the center of the macula lutea coincide with one another and positions of the center of the optic disc coincide with one another in all the images represented by the pieces of data as illustrated in FIG. 8C. In this position alignment method, enlargement and reduction and coordinate transform such as Affine transform are performed on individual pieces of data to perform position alignment. Also, position alignment may be performed using structures on the retina other than the center of the macula lutea and the center of the optic disc. For example, position alignment may be performed using information on an angle at which the retinal blood vessel runs instead of the center of the optic disc.

Then in step S27, the statistical data generation unit 936 generates statistical data of layer thicknesses of the plurality of examined eyes. The statistical data is generated as statistical data of layer thicknesses of each layer at each position on the retina, and is associated with information on the center of the macula lutea and the center of the optic disc. The generated statistical data is then stored in the storage unit 926 in step S28.

Comparison Map of Macula Lutea Portion

Figure 1A:
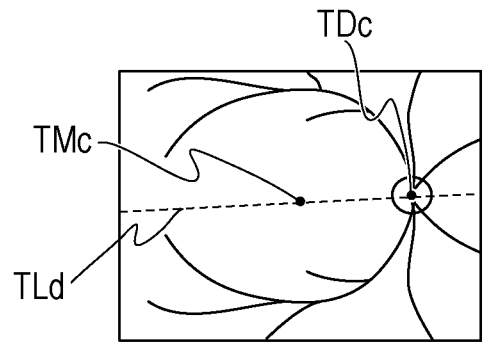
FIGS. 1A to 1C are diagrams illustrating a method for aligning a position of an image showing a layer thickness of a macula lutea portion with a position of an image represented by statistical data of layer thicknesses of healthy eyes in accordance with an embodiment of the present invention.
Figure 1B:
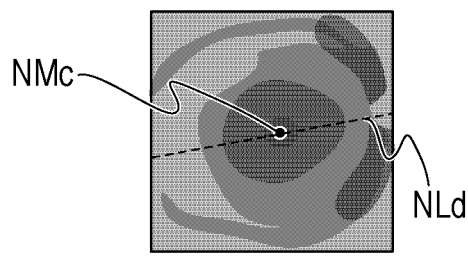
Figure 1C:
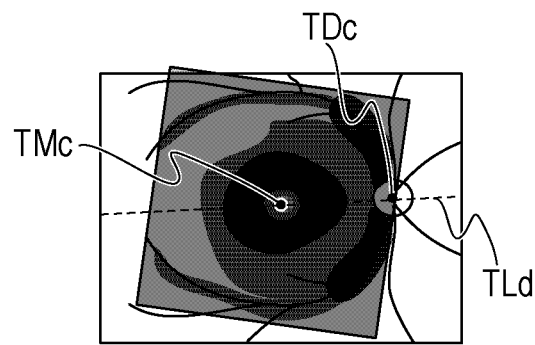

Referring next to FIGS. 1A to 1C, a method for generating the comparison map 4400 which is a feature of one aspect of the present invention will be described. A comparison map displays a result obtained by comparing a layer thickness of the eye being examined 107 with the above-described statistical data of layer thicknesses. The statistical data of layer thicknesses is pre-stored in the storage unit 926.

Figure 11:
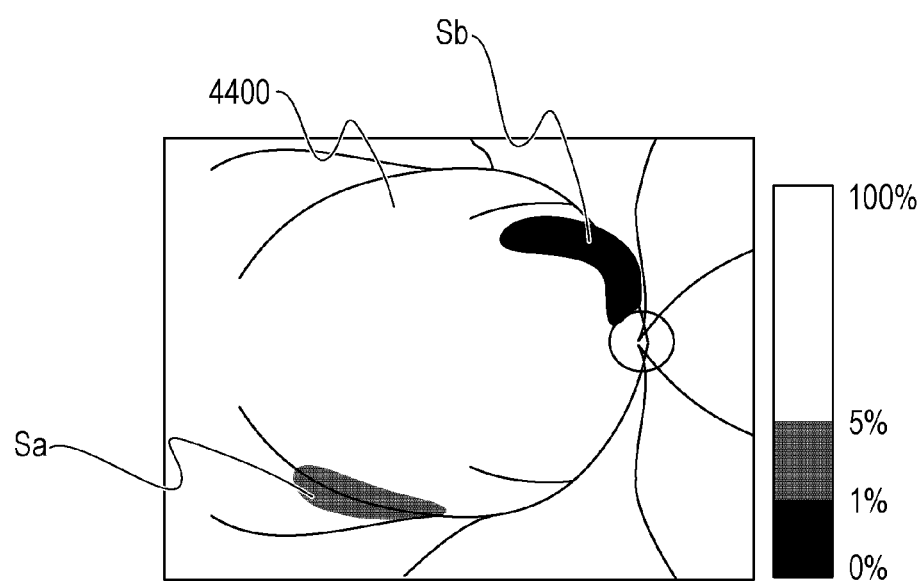
FIG. 11 is a diagram illustrating a display example of a result obtained by comparing a layer thickness of the macula lutea portion with the statistical data of layer thicknesses of healthy eyes.

Referring to FIG. 11, a configuration of the comparison map 4400 will be described. The comparison map 4400 is a comparison map that is superimposed on a front-view image. At portions Sa and Sb, the layer thickness is significantly smaller than the statistical data. The statistical data stored in the storage unit 926 includes layer thickness values corresponding to the bottom 5% and the bottom 1% relative to a distribution (normal distribution) of layer thicknesses of healthy eyes. In the case where the measured layer thickness of the eye being examined 107 is smaller than a layer thickness corresponding to the bottom 5%, the portion is displayed in a warning color such as yellow in the comparison map 4400. In the case where the measured layer thickness of the eye being examined 107 is smaller than a layer thickness corresponding to the bottom 1%, the portion is displayed in a danger-indicating color such as red in the comparison map 4400. The rest is not colored. Thus, the user can easily understand at which region on the retina the disease is progressing. Here, the example of the comparison map 4400 in which portions having a small layer thickness are colored has been described; however, portions having a large layer thickness may be colored. Alternatively, the comparison map 4400 may be colored in accordance with an amount of difference from the statistical data.

Referring next to FIG. 9, a flow of a process for creating the layer-thickness comparison map will be described. Because step S31 to step S35 are similar to step S11 to step S15 of the above-described process for generating the layer-thickness map, a description thereof will be omitted.

In step S36, the position alignment unit 935 reads the statistical data from the storage unit 926. In step S37, the position alignment unit 935 aligns an image showing a layer thickness of the eye being examined 107 with an image represented by the statistical data.

First, the position alignment unit 935 aligns the position of the center of the macula lutea TMc in the image of the eye being examined 107, which is illustrated in FIG. 1A, with the position of the center of the macula lutea NMc in the image represented by the statistical data, which is illustrated in FIG. 1B. This position alignment is performed by translating the image represented by the statistical data in the horizontal and vertical directions so that positions of the center of the macula lutea in both images substantially coincide with each other. Then, the position alignment unit 935 rotates the image represented by the statistical data about the center of the macula lutea so that inclinations of lines TLd and NLd extending from the center of the macula lutea toward the center of the optic disc become substantially equal to each other. As a result of these position alignments, the images represented by the pieces of data share a center-of-macula-lutea position TMc and a matching line TLd extending toward the center of the optic disc as illustrated in FIG. 1C. Thus, a highly reliable comparison map can be generated.

Figure 10A:
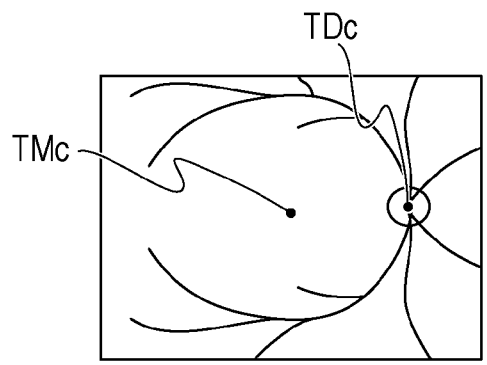
FIGS. 10A to 10C are diagrams illustrating a modification of the method for aligning a position of an image showing a layer thickness of the macula lutea portion with a position of an image represented by the statistical data of layer thicknesses of healthy eyes in accordance with the embodiment of the present invention.
Figure 10B:
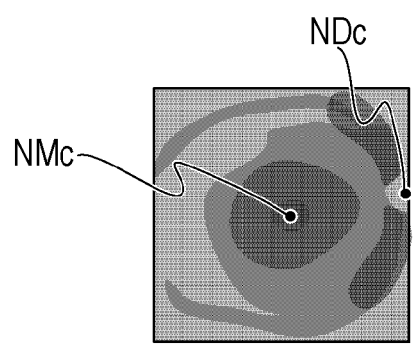
Figure 10C:
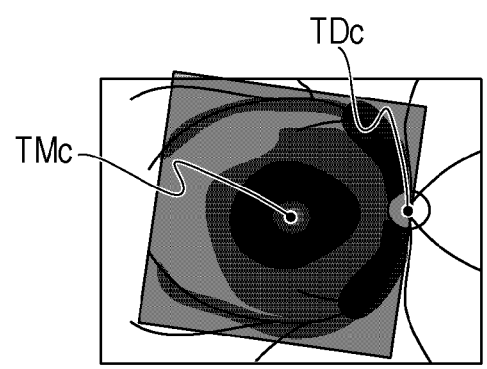

In another embodiment of position alinement, position alignment may be performed so that positions of the center of the macula lutea and positions of the center of the optic disc in the image of the eye being examined 107 and the image represented by the statistical data substantially coincide with each other as illustrated in FIGS. 10A to 10C. In this position alignment method, enlargement and reduction and coordinate transform such as Affine transform are performed on the statistical data to perform position alignment. Also, position alignment may be performed using structures on the retina other than the center of the macula lutea and the center of the optic disc. For example, position alignment may be performed using information on an angle at which the retinal blood vessel runs instead of the center of the optic disc.

Then in step S38, the comparison map generation unit 937 compares the layer thickness of the eye being examined 107 and the statistical data, and generates comparison map data on the basis of the result. In step S39, the display control unit 938 displays the comparison map 4400 on the macula lutea report screen 4000. The process then ends in step S40.

As described above, to create the comparison map according to this embodiment of the present invention, comparison is performed after position alignment has been performed on the basis of structures on the retina. Therefore, a highly accurate comparison map can be provided.

For example, in the case of observing the progress of glaucoma, a method for comparing a thickness of the optic nerve fiber layer (NFL) with the statistical data is generally used. Optic nerve fibers radially run from the optic disc portion, and are led to the proximity of the center of the macula lutea like an arc. Accordingly, in the case where the layer thickness of the optic nerve fiber layer is compared with the statistical data, it is important to perform position alignment so that running loci of the optic nerves substantially coincide with each other, and then to compare the obtained result with the statistical data. On the other hand, the positional relationship between the optic disc portion and the center of the macula lutea varies from person to person. A normalized angle between the optic disc portion and the center of the macula lutea greatly varies from person to person, and the running locus of the optic nerve fiber layer also changes depending on the angle. Accordingly, in the case where position alignment is performed by using only one piece of information (e.g., position of the center of the optic disc), portions in which the running loci of the optic nerve fiber layer do not coincide with each other may be compared. However, an aspect of the present invention can enable more accurate comparison as a result of more accurate position alignment.

An example of the comparison map which shows layer thickness comparison results at individual positions on the retina has been described here; however, the embodiment of the present invention can be applied to the case where a layer thickness in a region of a certain range on the retina is compared with the statistical data. For example, a 6-mm range from the central portion of the retina is divided into 9 sectors, and an average layer thickness is determined in each of the sectors. The average layer thickness of each sector is then compared with the statistical data, and the sector is colored on the basis of the comparison result. When the average in the sector is compared with the statistical data, position alignment can be performed using pieces of position information on the center of the macula lutea and on the center of the optic disc as in the above-described comparison map.

Configuration of Report Screen for Optic Disc Portion

Figure 12:
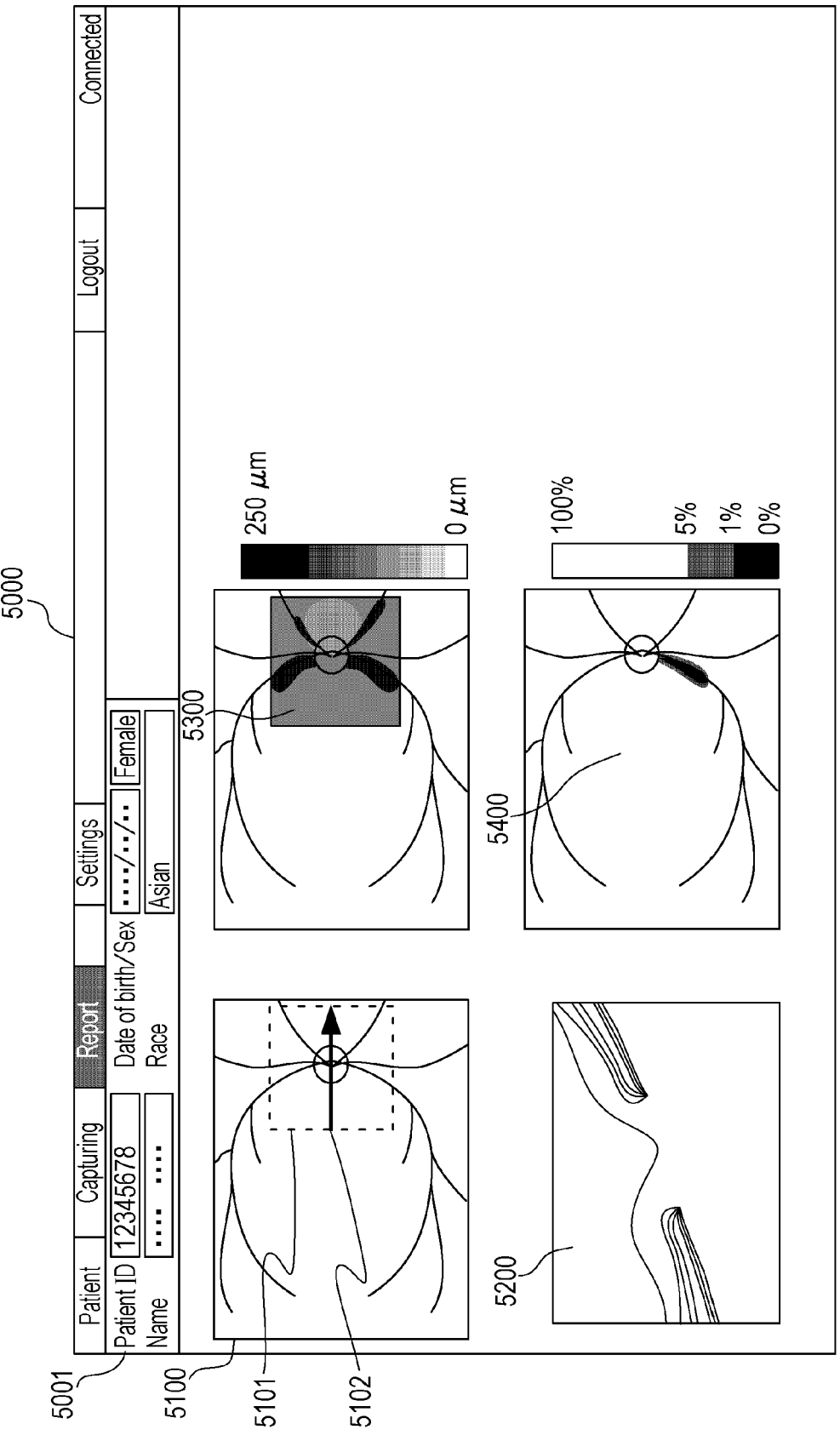
FIG. 12 is an illustrative diagram of a report screen that displays an analysis result obtained in the case where an image has been captured by focusing on an optic disc portion.

Referring to FIG. 12, an optic disc report screen 5000 according to this embodiment will be described. The optic disc report screen 5000 is a screen displayed on the display unit (i.e., a monitor) 928. The optic disc report screen 5000 is a screen on which an image of the eye being examined 107 that has been captured by selecting the optic-disc 3D mode with the scan mode selection button 2012, a measurement result, and a comparison result are checked in detail.

A patient information display portion 5001 displays information on a patient subjected to displaying in this screen, and displays, for example, the patient ID and the patient's name, date of birth, sex, and race. A front-view image display screen 5100 displays an SLO image or a projection image which is an image of the eye being examined 107 that has been reconstructed or reconfigured from the obtained tomographic image. A tomographic image display screen 5200 displays the obtained tomographic image. The locus of scanning performed when the tomographic image displayed on the tomographic image display screen 5200 is obtained is superimposed as an arrow 5102 on the front-view image display screen 5100. A frame 5101 displayed within the front-view image display screen 5100 indicates a range in which the tomographic image is obtained during capturing, and is a 6-mm×6-mm square centered at the optic disc.

A layer-thickness map 5300 and a comparison map 5400 are also displayed. These maps will be described in detailed below.

Layer-thickness Map of Optic Disc Portion

Because methods for generating and displaying a layer-thickness map of the optic disc portion are the same as the above-described methods for generating and displaying the layer-thickness map of the macula lutea portion, a description thereof is omitted.

Note that an NFL thickness map is generally displayed as a layer-thickness map of the optic disc portion for use in diagnosis of glaucoma. This is because NFL (optic nerve fiber layer) radially extends from the optic disc portion, and observation of the NFL thickness near the optic disc enables prediction of a position and a direction of a defect in the field of view in the entire retina.

Statistical Data of Optic Disc Portion

Figure 13A:
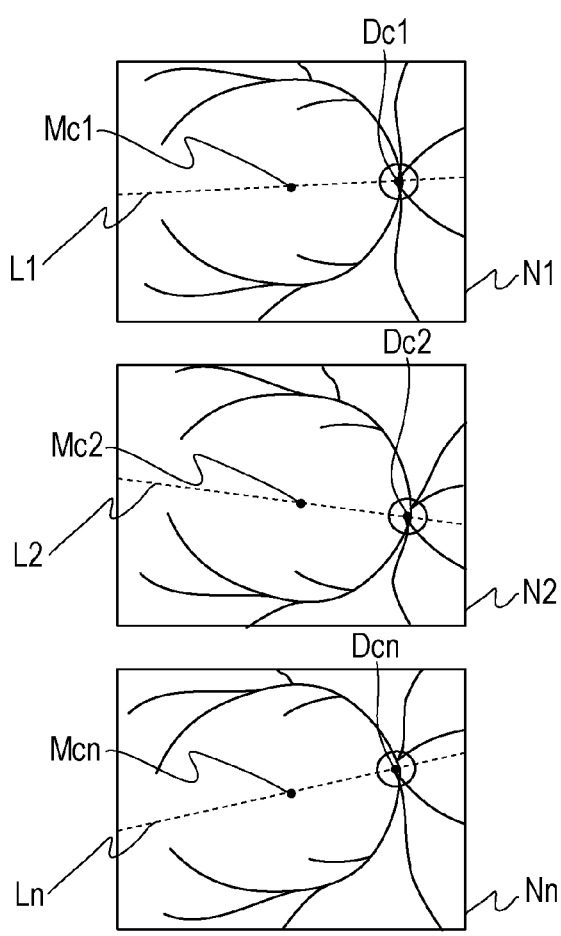
FIGS. 13A to 13C are diagrams illustrating a method for generating statistical data of layer thicknesses of the optic disc portion.
Figure 13B:
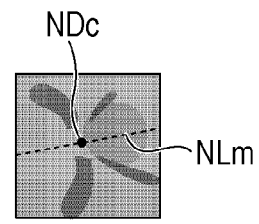
Figure 13C:
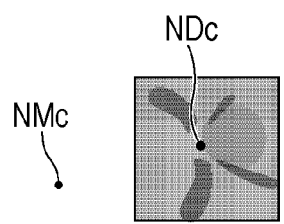

Referring next to FIGS. 13A to 13C, a method for generating statistical data for use in a comparison of a layer thickness of the optic disc portion will be described. The method for generating statistical data of the optic disc portion is substantially the same as the above-described method for generating statistical data of the macula lutea portion except for the position alignment method. This will be described in detail below.

As described above, when an image of the macula lutea portion is captured, a thickness of a layer including GCL is captured in general. Because GCL is distributed in a donut-like shape with respect to the macula lutea, position alignment is performed so that positions of the center of the macula lutea substantially coincide with each other. On the other hand, when an image of the optic disc portion is captured, a thickness of NFL is measured in general. Because NFL radially runs from the optic disc, position alignment is desirably performed so that positions of the center of the optic disc substantially coincide with each other. Thus, in the case where an image of the optic disc has been captured, position alignment is performed on the statistical data in the following manner.

The position alignment unit 935 performs position alignment on images showing layer thicknesses of a plurality of examined eyes. First, the position alignment unit 935 aligns positions of the center of the optic disc Dc1, Dc2, ..., Dcn illustrated in FIG. 13A. This position alignment is performed by translating the images represented by the pieces of data in the horizontal and vertical directions so that the positions of the center of the optic disc in all the images substantially coincide with one another. Then, the position alignment unit 935 aligns positions of the center of the macula lutea Mc1, Mc2, ..., Mcn. This position alignment is performed by rotating the images represented by the pieces of data about the center of the optic disc so that inclinations of lines L1, L2, ..., Ln extending from the center of the optic disc Dcn toward the center of the macula lutea Mcn are substantially equal to one another. As a result of these position alignments, all the images represented by the pieces of data share a center-of-optic-disc position NDc and a matching line NLm extending toward the center of the macula lutea as illustrated in FIG. 13B. Thus, highly reliable statistical data can be generated.

In another embodiment of position alinement, position alignment may be performed so that positions of the center of the macula lutea substantially coincide with one another and positions of the center of the optic disc substantially coincide with one another in all the images represented by the pieces of data as illustrated in FIG. 13C. In this position alignment method, enlargement and reduction and coordinate transform such as Affine transform are performed on each piece of data to perform position alignment.

Comparison Map of Optic Disc Portion

Figure 14A:
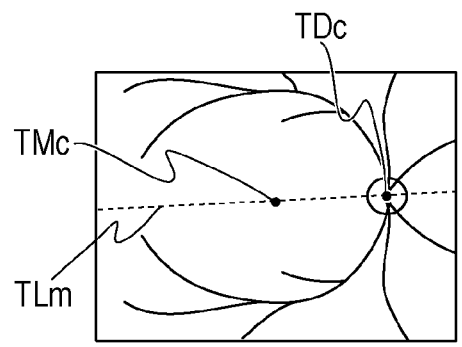
FIGS. 14A to 14C are diagrams illustrating a method for aligning a position of an image showing a layer thickness of the optic disc portion with a position of an image represented by the statistical data of layer thicknesses of healthy eyes in accordance with the embodiment of the present invention.
Figure 14B:
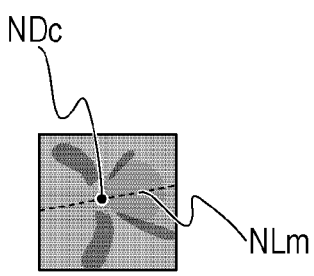
Figure 14C:
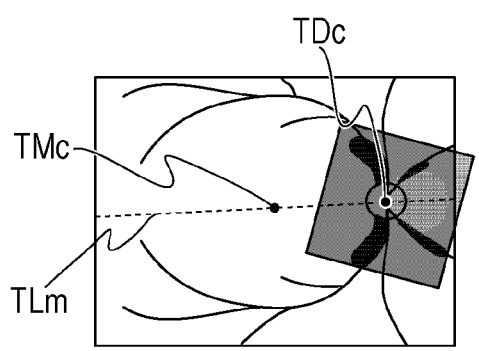

Referring next to FIGS. 14A to 14C, a method for generating the comparison map 5400 which is a feature of one aspect of the present invention will be described. The method for generating a comparison map of the optic disc portion is substantially the same as the above-described method for generating a comparison map of the macula lutea portion except for part of the position alignment method. This will be described in detail below.

As in the position alignment for the statistical data, position alignment is desirably performed so that positions of the center of the optic disc substantially coincide with each other when an image of the optic disc portion has been captured. Thus, in the case where an image of the optic disc portion has been captured, position alignment is performed on the statistical data in the following manner.

The position alignment unit 935 aligns the position of the center of the optic disc TDc in the image of the eye being examined 107 illustrated in FIG. 14A with the position of the center of the optic disc NDc in the image represented by the statistical data illustrated in FIG. 14B. This position alignment is performed by translating the image represented by the statistical data in the horizontal and vertical directions so that the positions of the center of the optic disc in both images substantially coincide with each other. Then, the position alignment unit 935 rotates the image represented by the statistical data about the center of the optic disc so that inclinations of lines TLm and NLm extending from the center of the optic disc toward the center of the macula lutea are substantially equal to each other. As a result of these position alignments, the images represented by the pieces of data share a center-of-optic-disc position TDc and a matching line TLm extending toward the center of the macula lutea as illustrated in FIG. 14C. Thus, a highly reliable comparison map can be generated.

Figure 15A:
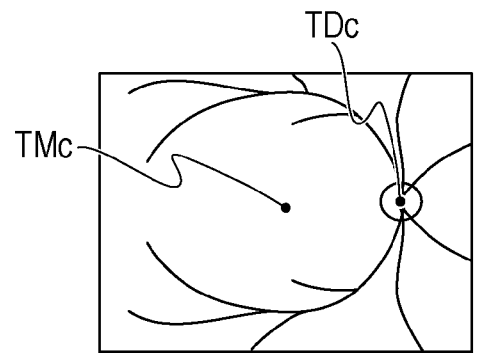
FIGS. 15A to 15C are diagram illustrating a modification of the method for aligning a position of an image showing a layer thickness of the optic disc portion with a position of an image represented by the statistical data of layer thicknesses of healthy eyes in accordance with the embodiment of the present invention.
Figure 15B:
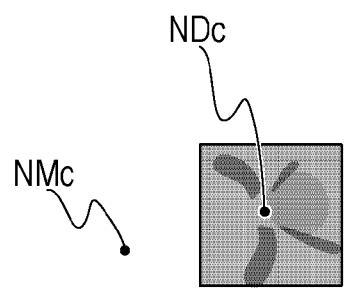
Figure 15C:
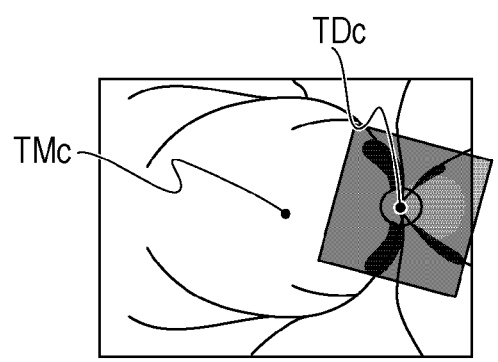

In another embodiment of position alinement, position alignment may be performed so that positions of the center of the macula lutea and positions of the center of the optic disc in the image of the eye being examined 107 and the image represented by the statistical data substantially coincide with each other as illustrated in FIGS. 15A to 15C. In this position alignment method, enlargement and reduction and coordinate transform such as Affine transform are performed on the statistical data to perform position alignment.

An example of the comparison map which shows layer thickness comparison results at individual positions on the retina has been described here; however, the embodiment of the present invention can be applied to the case where layer thicknesses on a predetermined locus on the retina are compared with the statistical data. For example, layer thicknesses are measured on a circular locus having a diameter of 3.45 mm centered at the optic disc. The layer thickness at each position on the circular locus is displayed in a graph as a layer thickness profile. The statistical data is then superimposed on this graph. When the statistical data is superimposed on the graph, position alignment is performed using pieces of position information on the center of the macula lutea and the center of the optic disc as in the above-described comparison map. In this way, the position at which the statistical data is superimposed can be adjusted.

Other Embodiments

While the embodiment has been described in detail above, the embodiment of the present invention can take a form of, for example, a system, an apparatus, a method, a program, or a storage medium. Specifically, the embodiment may be applied to a system including a plurality of devices, or to an apparatus including a single device.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to an aspect of the present invention, accuracy in comparison of a layer thickness of an eye being examined with layer thickness statistical data of healthy eyes can be improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-221088, filed Oct. 24, 2013, which is hereby incorporated by reference herein in its entirety.

What is claimed is:

1. An ophthalmological apparatus comprising:
a measurement unit configured to measure data of a layer thickness of a predetermined tissue of the eye being examined by analyzing tomographic images of the eye being examined;
a position identifying unit configured to identify positions of a first part and a second part in the measured data;
a storage unit configured to store statistical data of layer thicknesses of the predetermined tissue of a plurality of eyes that have been examined;
a position alignment unit configured to perform position alignment on the measured data of the eye being examined and the statistical data of layer thicknesses of the predetermined tissue of the plurality of eyes that have been examined which is stored in a storage unit, by comparing an inclination of a first line extending from the first part toward the second part with an inclination of a second line extending from the first part in the statistical data toward the second part in the statistical data; and
a comparison unit configured to compare the measured data of the eye being examined with the statistical data.

2. The ophthalmological apparatus according to claim 1, wherein
the position identifying unit is configured to identify, for each of the plurality of eyes that have been examined, positions of the first part and the second part, and
the statistical data of the layer thicknesses is obtained by performing position alignment using pieces of information regarding the positions of the first part and the second part of the plurality of eyes that have been examined.

3. The ophthalmological apparatus according to claim 1, further comprising
a display unit configured to display a result of the comparison performed by the comparison unit.

4. The ophthalmological apparatus according to claim 2, further comprising
a display unit configured to display a result of the comparison performed by the comparison unit.

5. The ophthalmological apparatus according to claim 1, wherein one of the first part and the second part is a center of macula lutea and the other is a center of optic disc.

6. The ophthalmological apparatus according to claim 2, wherein one of first part and the second part is the center of macula lutea and the other is a center of optic disc.

7. The ophthalmological apparatus according to claim 3, wherein one of first part and the second part is the center of macula lutea and the other is a center of optic disc.

8. The ophthalmological apparatus according to claim 4, wherein one of first part and the second part is the center of macula lutea and the other is a center of optic disc.

9. The ophthalmological apparatus according to claim 5, wherein
the position alignment unit is configured to
perform position alignment in horizontal and vertical directions so that the center of the macula lutea in the measured data of the eye being examined substantially coincides with the center of the macula lutea in the statistical data, and
perform position alignment in a rotational direction so that the inclination of the first line substantially coincides with the inclination of the second line after position alignment in horizontal and vertical directions was performed.

10. The ophthalmological apparatus according to claim 6, wherein
the position alignment unit is configured to
perform position alignment in horizontal and vertical directions so that the center of the macula lutea in the measured data of the eye being examined substantially coincides with the center of the macula lutea in the statistical data, and perform position alignment in a rotational direction so that the inclination of the first line substantially coincides with the inclination of the second line after position alignment in horizontal and vertical directions was performed.

11. The ophthalmological apparatus according to claim 7, wherein the position alignment unit is configured to perform position alignment in horizontal and vertical directions so that the center of the macula lutea in the measured data of the eye being examined substantially coincides with the center of the macula lutea in the statistical data, and perform position alignment in a rotational direction so that the inclination of the first line substantially coincides with the inclination of the second line after position alignment in horizontal and vertical directions was performed.

12. The ophthalmological apparatus according to claim 8, wherein the position alignment unit is configured to perform position alignment in horizontal and vertical directions so that the center of the macula lutea in the measured data of the eye being examined substantially coincides with the center of the macula lutea in the statistical data, and perform position alignment in a rotational direction so that the inclination of the first line substantially coincides with the inclination of the second line after position alignment in horizontal and vertical directions was performed.

13. The ophthalmological apparatus according to claim 5, wherein the position alignment unit is configured to perform position alignment in horizontal and vertical directions so that the center of the optic disc in the measured data of the eye being examined substantially coincides with the center of the optic disc in the statistical data, and perform position alignment in a rotational direction so that the inclination of the first line substantially coincides with the inclination of the second line after position alignment in horizontal and vertical directions was performed.

14. The ophthalmological apparatus according to claim 6, wherein the position alignment unit is configured to perform position alignment in horizontal and vertical directions so that the center of the optic disc in the measured data of the eye being examined substantially coincides with the center of the optic disc in the statistical data, and perform position alignment in a rotational direction so that the inclination of the first line substantially coincides with the inclination of the second line after position alignment in horizontal and vertical directions was performed.

15. The ophthalmological apparatus according to claim 7, wherein the position alignment unit is configured to perform position alignment in horizontal and vertical directions so that the center of the optic disc in the measured data of the eye being examined substantially coincides with the center of the optic disc in the statistical data, and perform position alignment in a rotational direction so that the inclination of the first line substantially coincides with the inclination of the second line after position alignment in horizontal and vertical directions was performed.

16. The ophthalmological apparatus according to claim 8, wherein the position alignment unit is configured to perform position alignment in horizontal and vertical directions so that the center of the optic disc in the measured data of the eye being examined substantially coincides with the center of the optic disc in the statistical data, and perform position alignment in a rotational direction so that the inclination of the first line substantially coincides with the inclination of the second line after position alignment in horizontal and vertical directions was performed.

17. A comparison method comprising:

measuring data of a layer thickness of a predetermined tissue of the eye being examined by analyzing tomographic images of the eye being examined;

identifying positions of a first part and a second part in the measured data;

performing position alignment on the data of the eye being examined and statistical data of layer thicknesses of the predetermined tissue of a plurality of eyes that have been examined, by comparing a first line extending from the first part toward the second part with a second line extending from the first part in the statistical data toward the second part in the statistical data; and comparing the data of the eye being examined with the statistical data.

18. A non-transitory storage medium storing thereon a program causing the comparison method according to claim 17 to be executed.

19. A processing apparatus comprising:

an acquiring unit configured to acquire first data of a first eye and second data of a second eye being different from the first eye; and an aligning unit configured to align the first data with the second data based on an inclination of a first line extending from one of a macula lutea and an optic disc to the other in the first data and an inclination of a second line extending from one of the macula lutea and the optic disc to the other in the second data.

20. The processing apparatus according to claim 19, wherein the aligning unit configured to align the first data with the second data so that the inclination of the first line becomes substantially coincide with the inclination of the second line.

* * * * *